(12) United States Patent
Sinha

(10) Patent No.: US 6,427,536 B1
(45) Date of Patent: Aug. 6, 2002

(54) METHOD AND SYSTEM FOR MEASURING ANISOTROPIC MATERIAL PROPERTIES

(75) Inventor: Arvind K. Sinha, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/459,810

(22) Filed: Dec. 13, 1999

(51) Int. Cl.[7] ............................................... G01N 29/04
(52) U.S. Cl. ........................... 73/606; 73/597; 73/602; 73/659
(58) Field of Search .................. 73/606, 602, 659, 73/643, 579, 597, 600

(56) References Cited

U.S. PATENT DOCUMENTS

| | | | | |
|---|---|---|---|---|
| 4,655,228 A | | 4/1987 | Shimure et al. | 128/660 |
| 4,995,260 A | * | 2/1991 | Deason et al. | 73/643 |
| 5,305,239 A | * | 4/1994 | Kinra | 73/602 |
| 5,351,544 A | * | 10/1994 | Endo et al. | 73/588 |
| 5,402,681 A | * | 4/1995 | Nakaso et al. | 73/602 |
| 5,533,399 A | * | 7/1996 | Gibson et al. | 73/579 |
| 5,955,669 A | * | 9/1999 | Egami | 73/579 |
| 5,955,671 A | * | 9/1999 | Gilmore et al. | 73/597 |
| 6,182,512 B1 | * | 2/2001 | Lorraine | 73/655 |

OTHER PUBLICATIONS

"Frequency Analysis", by R.B. Randall, Published by Bruel & Kajaer 1987, pp. 271–304.

* cited by examiner

*Primary Examiner*—Hezron Williams
*Assistant Examiner*—Jacques Saint-Surin
(74) *Attorney, Agent, or Firm*—Bracewell & Patterson LLP

(57) ABSTRACT

A method and system for determining material properties of a cross-section of an anisotropic sample material. An ultrasonic signal is applied to the surface of the anisotropic sample material, which comprises multiple constituent material layers, such that a characteristic medium wave is induced within each of the constituent materials. Each of these characteristic medium waves is sampled over a time interval to obtain a test waveform. This resultant test waveform is then spectrum analyzed utilizing cepstrum noise filtration, such that the material properties of said anisotropic sample material may be determined.

18 Claims, 3 Drawing Sheets

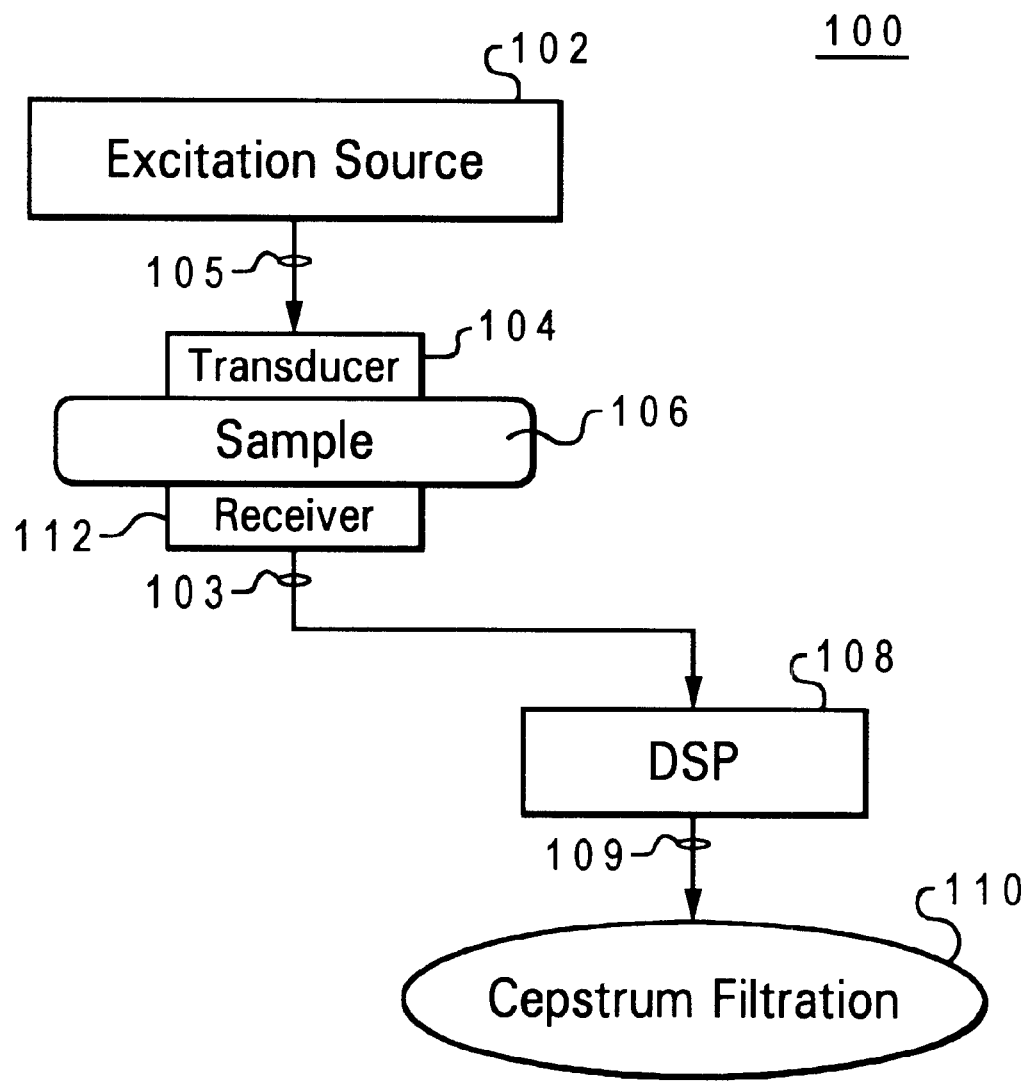
Fig. 1
(Amended)

METHOD AND SYSTEM FOR MEASURING ANISOTROPIC MATERIAL PROPERTIES

BACKGROUND OF THE INVENTION

1. Technical Field

The subject matter of the present invention relates to an improved method and system for measuring material properties of laminated circuit boards, and in particular to non-destructive ultrasonic measurement techniques. More particularly, the present invention relates to combining an ultrasonic circuit board material analysis with a cepstrum noise filtration process, thereby providing an accurate and efficient method and system for obtaining a material property profile for an anisotropic circuit board.

2. Description of the Related Art

Ultrasonic measurement techniques are sometimes utilized as a non-destructive alternative to traditional destructive material properties testing techniques. In order to evaluate the composition of an anisotropic circuit board in terms of its structural and chemical properties, it is necessary to analyze the material composition of the circuit board at various stages during circuit board fabrication. A test sample of the fabricated circuit board may be removed and subject to various testing procedures such as ASTM tensile tests. Such testing is economically inefficient both in terms of loss of usable circuit board material and in terms of the time consuming nature of such a two-step testing procedure.

One alternative to destructive circuit board testing techniques, are non-destructive material property characterizations performed utilizing ultrasonic waves. Such ultrasonic testing techniques are capable of characterizing the ultrasonic wave medium being observed. In the case of anisotropic circuit boards, this medium is composed of more than one element or material utilized as the supporting structure on which integrated circuit (IC) devices and modules are physically and electrically arranged and interconnected. Ultrasonic waves are induced into a test medium and observation of the composition of the test medium is accomplished utilizing ultrasonic waves reflection within the test medium.

The attenuation characteristic of reflected ultrasonic waves is often utilized as the parameter for discriminating among a layered isotropic material composition. As explained by Shimura et al. in U.S. Pat. No. 4,655,228, such an analysis relies on the fact that when an ultrasonic wave travels a distance, dz, over a given time interval (referred to hereinafter as "time-of-flight"), the sound pressure is attenuated in accordance with the following relation:

$$EXP\{-\alpha(z,f)dz\},$$

wherein $\alpha(z,f)$ varies as a function of location, z, and frequency, f.

However, due to the complexity involved in translating ultrasonic wave reflection within an anisotropic material, conventional ultrasonic material measurement procedures have suffered from problems associated with inadequate noise filtration.

It can therefore be appreciated that a need exists for a non-destructive method and system for obtaining a material property profile for an anisotropic circuit board, such that a reliably accurate and noise-free profile of material composition may be obtained.

SUMMARY OF THE INVENTION

It is therefore an object of the invention to provide an improved method and system for measuring material properties of laminated circuit boards, and in particular to non-destructive ultrasonic measurement techniques.

It is another object of the invention to provide a method and system for combining an ultrasonic circuit board material analysis with a cepstrum noise filtration process, thereby providing a accurate and efficient method and system for obtaining a material property profile for an anisotropic circuit board.

The above and other objects are achieved as is now described. A method and system for determining material properties of a cross-section of an anisotropic sample material are disclosed. An ultrasonic signal is applied to the surface of the anisotropic sample material, which comprises multiple constituent material layers, such that a characteristic medium wave is induced within each of the constituent materials. Each of these characteristic medium waves is sampled over a time interval to obtain a test waveform. This resultant test waveform is then spectrum analyzed utilizing cepstrum noise filtration, such that the material properties of said anisotropic sample material may be determined.

DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

FIG. 1 is a block diagram depicting a simplified signal processing system in accordance with a preferred embodiment of the present invention;

DETAILED DESCRIPTION OF A PREFERRED EMBODIMENT

Figure 2A:
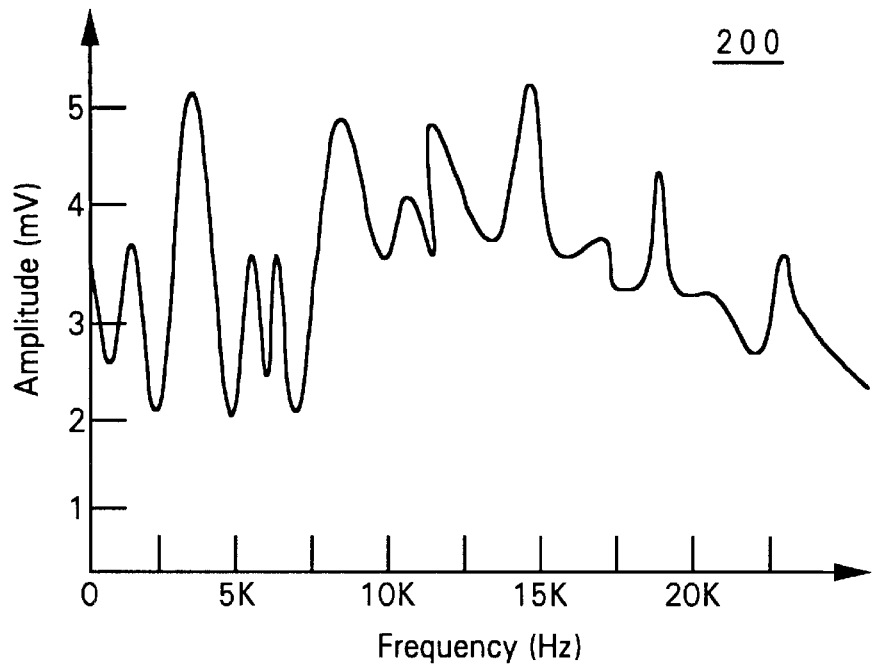
FIG. 2A illustrates a logarithmic spectrum of an ultrasonic signal sampled and stored in accordance with the teachings of the present invention.

The present invention provides a method and system for utilizing an innovative ultrasonic signal processing technique to measure material properties of laminated circuit boards. Earlier problems associated with ultrasonic material property measurement have been associated with obtaining a relatively noise free time-of-flight signal from which material property metrics may be obtained. Fundamental to the method and system of the present invention is a signal processing technique in which such noise is removed thereby rendering a spectrum from which material properties of the sample material may be discovered. Paraphrased from "spectrum", the term "cepstrum" is known in the art as a function for obtaining the inverse Fourier transform of a logarithmic spectrum. A detailed explanation and illustration of the mathematical calculations involved in performing a cepstrum analysis is provided by, R. B. Randall in "Frequency Analysis" (Bruel & Kjar, 1987), pages 271–281, which is incorporated herein by reference.

As explained further with reference to the figures, a method and system are disclosed herein for generating a relatively clear signal from a noise-buried signal utilizing cepstrum analysis. This improved method and system of signal processing is utilized to evaluate the material properties of laminated circuit boards in a non-destructive manner.

With reference now to the figures and in particular with reference to FIG. 1, a block diagram depicts a simplified signal processing system 100 in accordance with a preferred embodiment of the present invention. As seen in FIG. 1, signal processing system 100 includes an excitation source 102 which together with piezo-electric crystals 104 comprise a signal generator for applying an ultrasonic signal 105 to a surface 107 of an anisotropic sample material 106. In a preferred embodiment of the present invention anisotropic sample material 106 is a laminated circuit board consisting of several constituent materials. As separate layers and as a composite, these constituent materials have material properties having relevance with respect to circuit fabrication and related circuit board processing techniques.

Signal processing system 100 also includes a digital signal processor 108 and cepstrum filter 110 for sampling and analyzing internal medium signals 103 received from sample material 106. An analysis of sample material 106 is commenced when excitation source 102 generates ultrasonic signal 105 which triggers ultrasonic wave generation by piezo-electric crystals 104. Upon application of an ultrasonic wave to surface 107, an internal medium signal (not depicted) is induced into anisotropic sample material 106. The induced ultrasonic wave from ultrasonic signal 105 is applied to surface 107 and becomes an internal medium wave 103 as it traverses through the constituent materials which comprises sample material 106. While traveling through a cross-section of sample material 106, the original spectral characteristics such as frequency and phase of the induced ultrasonic signal are altered. In addition to experiencing frequency and phase skews, induced internal medium signal 103 may include echo signals resulting from reflection at material interface boundaries encountered through a cross-section of sample material 106.

As illustrated in FIG. 1, internal medium signal 103 is monitored and analyzed beginning at signal processor 108 which in the depicted example is a digital signal processor. In a preferred embodiment of the present invention, signal processor 108 samples internal medium signal 103 at a very high sampling rate of between 150 and 250 MHz. A test waveform 109 is constructed utilizing this high frequency sampling technique and may be saved, possibly as an ASCII file, in a signal bearing medium such as a magnetic or optical storage device within a computer system (not depicted) which collects input from signal processor 108. After digital signal processing in which test waveform 109 is obtained from internal medium signal 103, a cepstrum analysis module 110 determines spectral characteristics of test waveform 109. In an important feature of the present invention, cepstrum analysis module is utilized to determine the material properties of the anisotropic sample material 106.

FIG. 2A illustrates a logarithmic spectrum 200 of an ultrasonic signal sampled and stored in accordance with the teachings of the present invention. Logarithmic spectrum 200 is produced from a signal processing analysis performed on a recorded internal medium signal such as test waveform 109 of FIG. 1. As depicted in FIG. 2A, logarithmic spectrum 200 includes an enormous amount of noise in the form of signal distortions, harmonics, etc., resulting in a signal from which it is difficult to interpret material property information regarding the tested sample material.

Figure 2B:
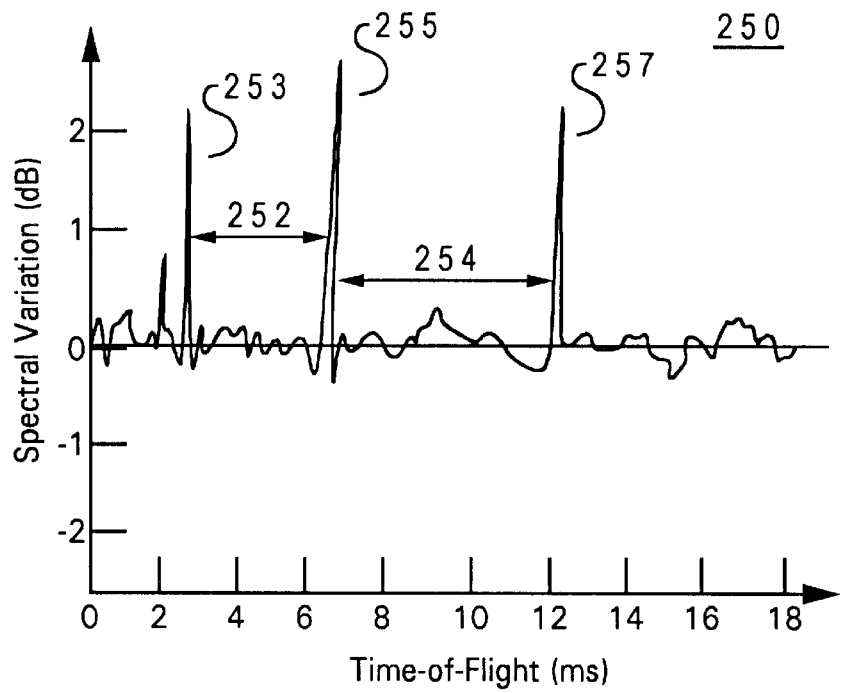
FIG. 2B depicts the cepstrum of the spectrum of FIG. 2A.

FIG. 2B depicts the cepstrum 250 of the spectrum of FIG. 2A which in a preferred embodiment of the present invention is utilized to determine critical signal characteristics such as peak-to-peak time-of-flight. Filtration such as that performed within cepstrum analysis module 110 of FIG. 1, result in the rendering of peaks 253, 255, and 257 which represent harmonics which characterize the arrival and departure of the internal medium signal to and from a particular material layer within the sample. In one embodiment of the present invention, the filtration utilized to render cepstrum 250 from logarithmic spectrum 200 is characterized by the following inverse Fourier transform:

$$C(\tau) = F^{-1}\{\log S(f)\},$$

wherein f represents the values on the frequency axis of FIG. 2A, and τ represents the values on the time axis of FIG. 2B.

Peak 253 may represent the arrival of an induced ultrasonic signal at the interface between two material layers within a laminated circuit board. As illustrated in FIG. 2B, the independent axis is measured in units of time. Therefore, the timespans 252 and 254 may be utilized to measure the time-of-flight for the induced ultrasonic signal between interfaces as marked by peaks 253, 255, and 257.

Figure 3:
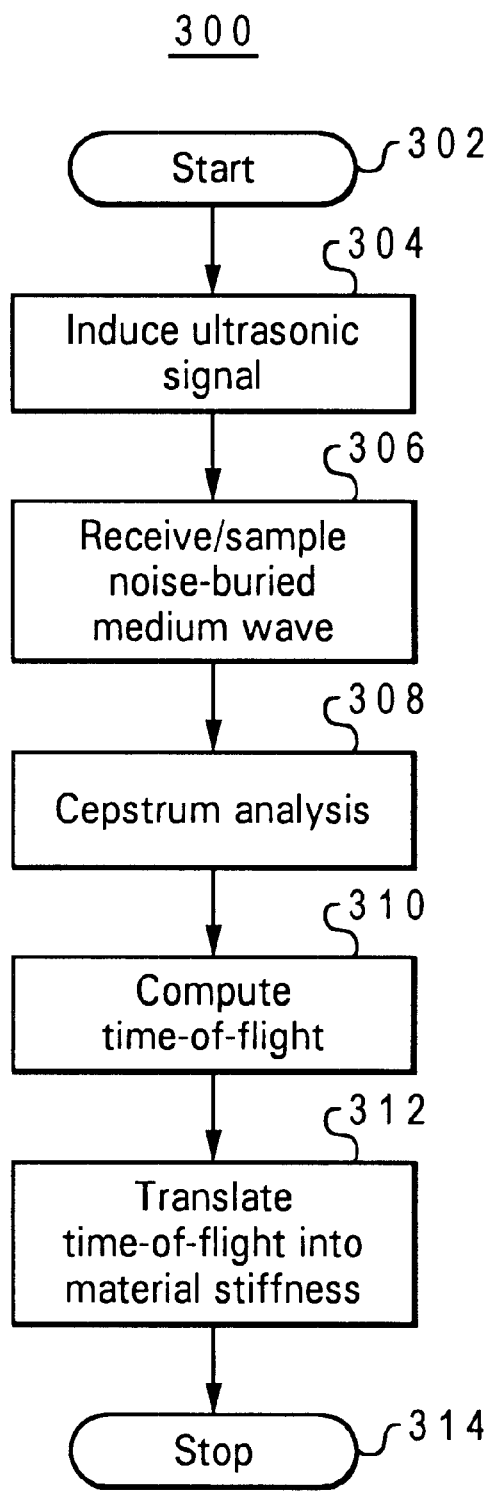
FIG. 3 is a simplified flow diagram illustrating one embodiment of the present invention in which cestrum analysis is utilized to evaluate the material properties of a laminated circuit board.

FIG. 3 is a simplified flow diagram illustrating a sequence of steps 300 in which cestrum analysis is utilized to evaluate the material properties of a laminated circuit board in accordance with the teachings of the present invention. The circuit board material evaluation commences at blocks 302 and 304 which illustrate the application of an ultrasonic signal to one surface of a laminated circuit board and resulting induction of an internal medium signal within a cross-section of the circuit board. As explained and illustrated with reference to the preceding figures, this internal medium signal will have spectral characteristics which will vary in accordance with the material properties, such as stiffness, of the circuit board constituent materials. A noise-buried signal is recovering by sampling the internal medium wave as shown at step 306.

The material property evaluation proceeds as illustrated at step 308 with a cepstrum analysis performed on the wave recovered at step 306. Although not explicitly depicted in FIG. 3, the wave recovered as shown at step 306 undergoes a preliminary spectrum analysis in which a logarithmic spectrum of the recovered wave is obtained. The cepstrum analysis involves a calculation of the inverse Fourier transform of the logarithmic spectrum of the recovered wave. As illustrated next at step 310, the cepstrum of the recovered wave is utilized to compute the time-of-flight as illustrated as timespans 252 and 254 in FIG. 2B. Finally, steps 312 and 314 depict the translation of the time-of-flight metric obtained at step 310 into a material stiffness parameter for the circuit board under test.

Preferred implementations of the invention include implementations as a computer system programmed to execute the method or methods described herein, and as a program product. According to the computer system implementation, sets of instructions for executing the method and system of the present invention are resident in a storage device such as the ROM or RAM of one or more computer systems. Until required by the computer system, the set of instructions may be stored as a computer-program product in another computer memory, for example, in a disk drive (which may include a removable memory such as an optical disk or floppy disk for eventual utilization in disk drive).

The computer-program product can also be stored at another computer and transmitted when desired to the user's workstation by a network or by an external communications network. One skilled in the art can appreciate that the physical storage of the sets of instructions physically changes the medium upon which it is stored so that the medium carries computer-readable information. The change may be electrical, magnetic, chemical, or some other physical change. While it is convenient to describe the invention in terms of instructions, symbols, characters, or the like, the reader should remember that all of these and similar terms should be associated with the appropriate physical elements. Thus, a method for implementing the steps described in association with FIG. 3 can be accomplished with a computer-aided device. In such a method, data stored in a memory unit of a data-processing system such as a data-processing system, can represent steps in a method for implementing a preferred embodiment of the present invention.

While the invention has been particularly shown as described with reference to a preferred embodiment, it will be understood by those skilled in the art that various changes in form and detail may be made therein without departing from the spirit and scope of the invention. It is therefore contemplated that such modifications can be made without departing from the spirit or scope of the present invention as defined in the appended claims.

What is claimed is:

1. A method for determining material properties of a cross-section of an anisotropic sample material, said method comprising the steps of:
    applying an ultrasonic signal to a first surface of said anisotropic sample material, such that an internal media signal is generated within said anisotropic sample material;
    sampling said internal media signal at a second surface of said anisotropic sample material over a time interval to obtain a test waveform;
    obtaining a spectral result of said test waveform, wherein said spectral result includes at least one peak representative of harmonics that characterize arrivals and departures of said internal media signal as said internal media signal travels through a particular material layer within said anisotropic sample material; and
    cepstrum analyzing said spectral result such that a time-of-flight between consecutive peaks is determined within said spectral result.

2. The method of claim 1, wherein said anisotropic sample material is a circuit board having a first outer surface and an opposing second outer surface, and wherein said applying step comprises the steps of:
    acoustically coupling a transducer to said first outer surface; and
    exciting said transducer, such that said ultrasonic signal is applied to said first outer surface.

3. The method of claim 2, wherein an ultrasonic receiver is acoustically coupled to said opposing second outer surface, and wherein said sampling step comprises the steps of:
    receiving said internal media signal at said ultrasonic receiver; and
    recording said internal media signal at a pre-determined sample rate in response to said receiving step, such that said test waveform is obtained.

4. The method of claim 3, wherein said recording step is preceded by the step of digitally processing said internal media signal.

5. The method of claim 1, wherein said anisotropic sample material comprises a plurality of constituent material layers, said method further comprising the steps of:
    applying said ultrasonic signal to said surface of said anisotropic sample material, such that a characteristic medium wave is induced within each of said constituent materials; and
    spectrum analyzing said characteristic medium wave induced within each of said constituent materials.

6. The method of claim 5, wherein said step of spectrum analyzing said characteristic wave induced within each of said constituent materials comprises the step of measuring the speed of said characteristic medium wave for each of said constituent materials.

7. The method of claim 1, wherein said cepstrum analyzing step comprises obtaining a cepstrum, $C(\tau)$, of said spectral result in accordance with the relation:

$$C(\tau)=F^{-1}\{\log S(f)\},$$

wherein S(f) is a function designating said spectral result.

8. The method of claim 1, wherein said cepstrum analyzing step comprises the step of logarithmically converting said spectral result, such that a logarithmic spectrum of said test waveform is obtained.

9. The method of claim 8, further comprising the step of utilizing said logarithmic spectrum of said test waveform to determine a time-of-flight of said characteristic medium wave for each of said constituent materials.

10. The method of claim 9, further comprising the step of converting said determined time-of-flight of said characteristic medium wave for each of said characteristic materials into a corresponding material stiffness parameter.

11. A system for determining material properties of a cross-section of an anisotropic sample material, said system comprising:
    a signal generator for applying an ultrasonic signal to a first surface of said anisotropic sample material, such that an internal media signal is generated within said anisotropic sample material;
    an ultrasonic receiver for receiving said internal media signal, wherein said ultrasonic receiver is coupled to a second surface of said anisotropic sample material opposing said first surface;
    a signal processor coupled to said ultrasonic receiver for sampling said internal media signal over a time interval to obtain a test waveform; and
    a spectrum analyzer for obtaining a spectral result of said test waveform, wherein said spectral result includes at least one peak representative of harmonics that characterize arrivals and departures of said internal media signal as said internal media signal travels through a particular material layer within said anisotropic sample material; and
    digital signal processing means for cepstrum analyzing said spectral result to determine a time-of-flight between a plurality of peaks within said spectral result such that the material properties of said anisotropic sample material are determined.

12. The system of claim 11, wherein said anisotropic sample material is a circuit board having a first outer surface and an opposing second outer surface, and wherein said signal generator comprises:
    a first piezo-electric transducer acoustically coupled to said first outer surface of said circuit board; and
    an excitation signal applied to said first piezo-electric transducer, such that said ultrasonic signal is applied to said first outer surface of said circuit board.

13. The system of claim 12, wherein said circuit board has a first outer surface and an opposing second outer surface, and wherein said ultrasonic receiver comprises a second piezo-electric transducer acoustically coupled to said second outer surface for receiving and translating said internal media signal.

14. The system of claim 11, wherein said signal processor coupled to said ultrasonic receiver includes means for recording said internal media signal at a pre-determined sample rate in response to said receiving said internal media signal, such that said test waveform is obtained.

15. The system of claim 11, wherein said digital signal processing means comprises computation means for logarithmically converting said spectral result, such that a logarithmic spectrum of said test waveform is obtained.

16. The system of claim 15, wherein said digital signal processing means further comprises computation means for determining the inverse Fourier transform of said logarithmic spectrum.

17. The system of claim 15, wherein said digital signal processing means further comprises computation means for determining a time-of-flight of said characteristic medium wave for each of said constituent materials from said logarithmic spectrum of said test waveform.

18. The system of claim 17, wherein said digital signal processing means further comprises computation means for translating said determined time-of-flight of said characteristic medium wave for each of said constituent materials into a corresponding material stiffness parameter.

* * * * *